United States Patent
Balicki et al.

(10) Patent No.: US 12,295,679 B2
(45) Date of Patent: May 13, 2025

(54) ROBOTIC POSITIONING OF A DEVICE

(71) Applicant: KONINKLIJKE PHILIPS N.V., Eindhoven (NL)

(72) Inventors: Marcin Arkadiusz Balicki, Cambridge, MA (US); Alexandru Patriciu, Belmont, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 439 days.

(21) Appl. No.: 17/773,644

(22) PCT Filed: Nov. 3, 2020

(86) PCT No.: PCT/EP2020/080827
§ 371 (c)(1),
(2) Date: May 2, 2022

(87) PCT Pub. No.: WO2021/089550
PCT Pub. Date: May 14, 2021

(65) Prior Publication Data
US 2022/0378526 A1    Dec. 1, 2022

Related U.S. Application Data

(60) Provisional application No. 62/931,279, filed on Nov. 6, 2019.

(30) Foreign Application Priority Data

Nov. 19, 2019  (EP) ..................................... 19209920

(51) Int. Cl.
*A61B 34/30*        (2016.01)
*A61B 34/10*        (2016.01)
(Continued)

(52) U.S. Cl.
CPC .............. *A61B 34/30* (2016.02); *A61B 34/10* (2016.02); *A61B 34/20* (2016.02); *A61B 90/37* (2016.02);
(Continued)

(58) Field of Classification Search
CPC ......... A61B 34/30; A61B 34/10; A61B 34/20; A61B 90/37; A61B 2034/107;
(Continued)

(56) References Cited

U.S. PATENT DOCUMENTS

| 10,751,133 B2 * | 8/2020 | Toporek .................. A61B 34/20 |
| 2012/0289777 A1 * | 11/2012 | Chopra ................ A61B 5/6852 |
| | | 382/128 |

(Continued)

FOREIGN PATENT DOCUMENTS

| JP | 2014104530 A | 6/2014 |
| WO | 2017/115227 A1 | 7/2017 |
| WO | 2019/204699 A1 | 10/2019 |

OTHER PUBLICATIONS

International Search Report and Written Opinion Dated Jan. 22, 2021 For International Application No. PCT/EP2020/080827 Filed Nov. 3, 2020.

(Continued)

*Primary Examiner* — Jonathan T Kuo

(57) ABSTRACT

The present invention relates to robotic device positioning. By extending the robotic arm into the surgical field, a system is provided that automatically aligns an instrument following a plan, e.g., surgical plan, using only instrument tracking feedback. No tracking markers on the robot are required.

15 Claims, 4 Drawing Sheets

(51) Int. Cl.
    *A61B 34/20* (2016.01)
    *A61B 90/00* (2016.01)
    *B25J 9/16* (2006.01)

(52) U.S. Cl.
    CPC ........... *B25J 9/1653* (2013.01); *B25J 9/1666* (2013.01); *A61B 2034/107* (2016.02); *A61B 2034/2051* (2016.02); *A61B 2034/2055* (2016.02); *A61B 2034/2063* (2016.02); *A61B 2034/2065* (2016.02); *A61B 2090/3764* (2016.02); *A61B 2090/378* (2016.02)

(58) Field of Classification Search
    CPC .... A61B 2034/2051; A61B 2034/2055; A61B 2034/2063; A61B 2034/2065; A61B 2090/3764; A61B 2090/378; A61B 34/32; B25J 9/1653; B25J 9/1666
    See application file for complete search history.

(56) References Cited

U.S. PATENT DOCUMENTS

| | | |
|---|---|---|
| 2014/0180290 A1 | 6/2014 | Otto |
| 2015/0164607 A1 | 6/2015 | Ruijters |
| 2018/0000546 A1* | 1/2018 | Crawford ............... A61B 90/96 |
| 2018/0185100 A1 | 7/2018 | Weinstein |
| 2019/0000561 A1 | 1/2019 | Decker |
| 2020/0038116 A1* | 2/2020 | Toporek ................. A61B 34/20 |
| 2020/0197108 A1 | 6/2020 | Usui |
| 2020/0229879 A1* | 7/2020 | Magaraggia ........... A61B 34/30 |

OTHER PUBLICATIONS

Blausen.com staff (2014). "Medical gallery of Blausen Medical 2014". WikiJournal of Medicine 1 (2). DOI:10.15347/wjm/2014. 010. ISSN 2002-4436 https://en.wikiversity.org/wiki/WikiJournal_of_Medicine/Medical_gallery_of_Blausen_Medical_2014.

* cited by examiner

ROBOTIC POSITIONING OF A DEVICE

CROSS REFERENCE TO RELATED APPLICATIONS

This application is the U.S. National Phase application under 35 U.S.C. § 371 of International Application No. PCT/EP2020/080827 filed Nov. 3, 2020, which claims the benefit of U.S. Provisional Patent Application No. 62/931,279 filed Nov. 6, 2019 and European Patent Application Number 19209920.8 filed Nov. 19, 2019. These applications are hereby incorporated by reference herein.

FIELD OF THE INVENTION

The present invention relates to instrument positioning. In particular, the present invention relates to a system for instrument positioning, a method of controlling a system for instrument positioning, a computer program element, and a computer readable medium.

BACKGROUND OF THE INVENTION

Robotic device positioning has become more common in applications including e.g., surgical instrument guidance, manufacturing and machine operations, such as planes, construction machinery, for drilling, nailing, etc. Robotic solutions typically rely on an external tracking system to locate the robot and to establish a robot to object reference frame (e.g., patient reference frame) with optical markers fixed rigidly to an object of interest, e.g., a patient or an object to be drilled. An example of the robotic solutions can be found in US 2015/164607 A. However, the reference frame is prone to accidental shifts and obstructions, decreasing object tracking accuracy and increasing the risk of registration error.

US 2018/0000546 discloses a medical robot system, including a robot coupled to an actuator element with the robot configured for controlled movement and positioning.

US 2018/0185100 discloses systems and methods for surgical navigation providing mixed reality visualizations. The mixed reality visualizations depict virtual images in conjunction with real objects to provide improved visualization to users.

WO 2019/204699 discloses methods and systems for controlling a robotic arm, including tracking a motion of a handheld device using a motion tracking system and controlling a robotic arm to adjust at least one of a position and an orientation of an end effector of the robotic arm based on the tracked motion of the handheld device.

SUMMARY OF THE INVENTION

The invention is defined by the claims.

There may be a need to improve robotic device positioning.

The object of the present invention is solved by the subject-matter of the independent claims, wherein further embodiments are incorporated in the dependent claims. It should be noted that the following described aspects of the invention apply also for the system, the method, the computer program element, and the computer readable medium.

According to a first aspect of the present invention, a system is provided for instrument positioning. The system comprises a robotic system with a robotic arm having four or more degrees of freedom (DOF) of control and a system controller with an interface unit. The robotic arm comprises an instrument interface connectable to an instrument. The interface unit of the system controller is configured to provide sensor data comprising pose information of the instrument and target position with respect to an object. The pose information of the instrument comprises location and orientation of the instrument. The interface unit of the system controller is further configured to provide image data at the target position. A target trajectory is planned in the image data for positioning the instrument to the target position. The system controller is configured to transfer the pose information of the instrument and the planned target trajectory into an object coordinate system. The system controller is further configured to calculate a positional error between the tracked pose information of the instrument and the planned target trajectory. The system controller is further configured to transfer the positional error into a robot coordinate system of the robotic system for controlling the robotic arm to align the instrument with the planned target trajectory. The positional error comprises at least one of a translational error and a rotational error.

In other words, a system is provided that comprises four or more degrees of freedom robotic guidance arm for instrument positioning, which may be used for a hybrid operating room environment with integrated surgical navigation. The system uses pose information, i.e. location and orientation, of an instrument to provide feedback to a robotic system in maintaining a trajectory of the instrument with respect to a target trajectory planned by a user, e.g., a surgeon. Using instrument tracking as a direct feedback to achieve alignment with planned trajectory does not require any manual registration. The proposed system may be based on 4-DOF or 5-DOF device position feedback without additional tracking bodies on the robot.

In some examples, the proposed system may be used as surgical instrument guidance system.

In some examples, the proposed system may be applied in manufacturing for alignment of parts or machine operation such as planes, construction machinery, etc., where drilling, nailing, or concentric alignment is common.

The instrument has an elongated shape. The system controller is configured to control the robotic arm during a first motion of the robotic arm for each new targeting session to move the instrument in a predefined movement to generate a rough six degrees of freedom registration between the object coordinate system and the robot coordinate system. The predefined movement comprises a predefined rotational movement.

Optionally, the predefined movement may also comprise a predefined translational movement.

In other words, in case when only 4-DOF or 5-DOF instrument tracking is available: either on instrument axis inserted into the instrument interface, e.g., needle guide, or on instrument interface axis attached to the robotic arm, an approximate registration method is used to facilitate the alignment, because the object of interest, e.g., a patient, and robot base are typically static relative to each other during a short treatment time. The location of the instrument interface is also known relative to the robotic arm. The rough six degrees of freedom registration between the object coordinate system and the robot coordinate system is generated based on two pose information of the instrument and two pose information of the robotic arm before and after the movement. This will be explained hereafter and particularly with respect to the exemplary embodiments illustrated in FIGS. 3A and 3B.

The first motion of the robotic arm automatically initiates the rough registration process. Generally, assuming the motion of the robotic system and the instrument tracking feedback can be synchronized precisely, the predefined rotational movement for rough registration may be arbitrary, as long as it includes a large rotation, as larger angles lead to more accurate registration. It may also be possible to add arbitrary translation as well. This feature may be used in real-time to update or verify that the registration has not changed due to patient movement relative to the robotic system. Accordingly, the system controller may perform the rough registration automatically, avoiding any input from a user or adding time to the procedure.

According to an embodiment of the present invention, the sensor data comprises real-time pose information of the instrument with respect to the target position. The system controller is configured to calculate a real-time positional error between the tracked pose information of the instrument and the planned target trajectory and transfer the real-time positional error into the robot coordinate system of the robotic system for iteratively controlling the robotic arm to align the instrument with the planned target trajectory.

In other words, the real-time instrument position feedback may be used to iteratively move the instrument mounted in the instrument interface to align with the target trajectory for precise alignment.

In an example, during the alignment, the system controller may be configured to keep the height of the instrument interface constant relative to the patient, table, imaging axis, robot base, initial tool location, or other physical or virtual reference. This height constraint may provide safer and more intuitive robot behavior. Once aligned, the surgeon could lower the robotic arm along the guide axis and, if needed, command robot to align to target.

According to an embodiment of the present invention, the system controller is further configured to apply the rough six degrees of freedom registration for controlling the robotic arm to align the instrument with the planned target trajectory, when the sensor data does not comprises the pose information of the instrument.

The resulting registration process may be sufficient for positioning of the instrument near the desired trajectory in open loop fashion e.g., when outside of the tracking volume. Thus, as a further option, the system controller may be further configured to control the robotic arm to align the instrument with the planned target trajectory based on the rough six degrees of freedom registration, if the sensor data does not comprise the pose information of the instrument, e.g. when outside the tracking volume. Once the device is visible in the tracking system, then the system controller may use the pose information of the instrument to iteratively servo to the final high-accuracy alignment.

According to an embodiment of the present invention, the system further comprises a tracking system configured to obtain the sensor data comprising the pose information of the interventional instrument and the target position of the object of interest. The tracking system comprises at least one of: an optical tracking system, an electromagnetic tracking system, and an acoustic tracking system.

The optical tracking system may use one or more cameras arranged inside the imaging room for tracking pose information of the instrument. The one or more cameras may be capable of detecting infrared light, visible light, and/or near infrared light. Camera-tracked markers may be attached to the instrument.

Electromagnetic (EM) tracking systems are based on the principle of mutual induction, in which a field generator produces a known EM field to localize small EM sensors placed within the tracking volume. EM trackers have gained popularity due to their freedom from line-of-sight restrictions, small sensor size, and convenience of use. As a result of their sub-millimeter size, sensors can easily be placed inside the tip of the instrument.

Acoustic tracking devices employ high frequency (e.g., 20 kHz or greater) ultrasonic sound waves in the form of time-to-flight transducers/sensors or phase-referent systems.

As will be readily known to a person skilled in the art, the tracking system could simultaneously track markers on the instrument as well as markers on the object. Thus, the tracking system can create a registration between the object coordinate system and the tracking coordinate system.

According to an embodiment of the present invention, the tracking system is located on or inside a detector of the image acquisition system.

In an example, the tracking system, such as a camera, is attachable to the detector of the imaging acquisition system. For example, a camera may be temporally attached to a predefine position on or inside the detector of the imaging acquisition system during image acquisition, and detached from the detector after image acquisition.

In an example, the tracking system may be an integrated part of the detector.

Locating the tracking system on or inside a detector of the imaging acquisition system may allow inherently spatially registering the tracking coordinate system to an image coordinate system. This may alleviate the need to e.g. independent track and register the tracking coordinate system of an external tracking system to the image coordinate system.

According to an embodiment of the present invention, the system further comprises an image acquisition system configured to acquire the image data at the target position of the object of interest. The image acquisition system comprises at least one of: an X-ray imaging device, an ultrasound imaging device, and a magnetic resonance imaging device.

In other words, the instrument positioning system may be implemented in different imaging modalities.

According to an embodiment of the present invention, the robotic arm comprises a mechanical Remote-Center-of-Motion, RCM, mechanism having at least one degree of freedom of rotational control. The instrument interface is mounted on the RCM mechanism.

As used herein, the term "RCM" refers to a remote fixed point, with no physical revolute joint over there, around which a mechanism or part of it can rotate.

The RCM may be translated robotically by using a translational module. The inclusion of an RCM may minimize overall joint motions, producing ergonomic robot configurations and predictable motions for improved user interface, especially when executing Cartesian rotations. It may allow the instrument to be translated to an entry point, by predominantly actuating the translation module, and then rotated to align, using one or more distal joints, i.e. RCM. The last link shape may be optimized so that the instrument interface is closer to the RCM, enabling the positioning of the instrument interface close to the object and facilitate the use of short instruments.

According to an embodiment of the present invention, the system controller is configured to control the robotic arm to align the instrument with the planned target trajectory while the instrument translating in a safety plane for preventing collisions.

In an example, the safety plane may be a plane above and parallel to the table. For example, the safety plane may be defined by XY plane of the robot and the current robot guide position. Alternatively, the safety plane location may be defined as: relative to the tip of the instrument, and then transformed into the robot coordinate system, relative to the closet point on the instrument to the target trajectory with some reasonable constraints, such that point is not too far from the robot guide, or relative to the entry point.

More generally, the safety plane may be any plane defined to prevent robot collisions, such as robot colliding with the object to be examined, the robot itself, and related equipment. In other words, the safety plane causes the robot to move in a predictable fashion to prevent robot collisions.

According to an embodiment of the present invention, the sensor data comprises pose information of the robotic arm.

In other words, a hybrid feedback control may be employed that includes both robot end-effector tracking and device tracking feedback. This would allow for rough alignment with less precise robot tracking (e.g., without the instrument in the guide), and once the device is visible in the cameras and is near the target, then the system controller may use the pose information of the instrument to servo the final high-accuracy alignment. According to an embodiment of the present invention, the instrument comprises an interventional instrument.

According to an embodiment of the present invention, the interventional instrument comprises at least one of: an injection needle, an interventional catheter, and an interventional laser device.

According to a second aspect of the present invention, a method is provided for controlling a system as described above and below, comprising the following steps:
  a) receiving, by an interface unit of a system controller of the system, sensor data comprising pose information of an instrument with respect to a target position relative to an object, wherein the pose information of the instrument comprises location and orientation of the interventional instrument;
  b) receiving, by the interface unit of the system controller, image data at the target position, wherein a target trajectory is planned in the image data for positioning the instrument to the target position; and
  c) transferring, by a system controller of the system, the pose information of the instrument and the planned target trajectory into an object coordinate system, calculating a positional error between the tracked pose information of the instrument and the planned target trajectory; and transferring the positional error into a robot coordinate system of the robotic system for controlling the robotic arm to align the instrument with the planned target trajectory, wherein the positional error comprises at least one of a translational error and a rotational error.

According to a third aspect of the present invention, a computer program element for controlling an apparatus, which, when being executed by a processing unit, is adapted to perform the method as described above and below.

According to a fourth aspect of the present invention, a computer readable medium having stored the program element.

As used herein, the term "elongated" is used in its usual meaning, i.e. that the length dimension is larger than the width or diameter of the instrument. As an example, the elongated instrument may be a needle-like instrument.

As used herein, the term "instrument" may refer to a medical device, such as surgical tools, medical tools, biomedical tools, and diagnostic instruments. In some examples, the instrument may refer to an instrument for machine operation, such as an instrument for drilling, nailing, and concentric alignment.

As used herein, the term "object of interest" may refer to a patient, a human subject, or an animal subject. In some examples, the object of interest may refer to an object in manufacturing and machine operations, e.g., an object to be drilled, nailed, etc.

As used herein, the term "system controller" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality. The system controller may include consumer electronics devices, smart phones, tablet personal computers, wearable computing devices, personal digital assistants (PDAs), laptop computers, and/or any other like physical computing device that is capable of providing the described functionality.

As used herein, the term "instrument interface" may refer to a mechanical part to receive the instrument for robotic device positioning. For example, the instrument interface may be a needle guide. A surgical device, such as an injection needle, may be inserted and fixed in the needle guide.

As used herein, the term "unit" may refer to, be part of, or include an ASIC, an electronic circuit, a processor (shared, dedicated, or group) and/or memory (shared, dedicated, or group) that execute one or more software or firmware programs, a combinational logical circuit, and/or other suitable components that provide the described functionality.

Throughout this description, reference is made to different coordinate systems. The coordinate systems may be Cartesian, polar, spherical, cylindrical tetragonal, hexagonal, or any other three-dimensional (3D) co-ordinate system as discussed above. The coordinate systems as referred to herein below are now defined.

The term "object coordinate system" refers to a coordinate system where positions are defined relative to an origin that is a pre-selected point associated with the object, and having a relative position therewith that remains constant. For example, if the object is a patient, the term "object coordinate system" may also be referred to as patient coordinate system. The object coordinate system may for example be a Cartesian coordinate system having orthogonal axes, xyz, which may be defined with respect to the pre-selected point thereof, and may use natural language relative positioning terms such as left, right, up, down, forwards and backwards, to identify locations with respect to the pre-selected point. Alternatively, polar coordinates may be used to define positions in virtual space with respect to the pre-selected point associated with the object. Alternatively, any other 3D co-ordinate system may be used. Similarly, the term "robot coordinate system" refers to a coordinate system where positions are defined relative to an origin that is a pre-selected point associated with the robot, and having a relative position therewith that remains constant. The robot coordinate system may for example be a Cartesian coordinate system having orthogonal axes, xyz, which may be defined with respect to the pre-selected point thereof, and may use natural language relative positioning terms such as left, right, up, down, forwards and backwards, to identify locations with respect to the pre-selected point. Alternatively, polar coordinates may be used to define positions in virtual space with respect to the pre-selected point associated with the robot. Alternatively, any other 3D co-ordinate system may be used.

Similarly, the term "tracking coordinate system" refers to a coordinate system where positions are defined relative to an origin that is a pre-selected point associated with the tracking system and having a relative position therewith that remains constant. The tracking coordinate system may for example be a Cartesian coordinate system having orthogonal axes, xyz, which may be defined with respect to the pre-selected point thereof, and may use natural language relative positioning terms such as left, right, up, down, forwards and backwards, to identify locations with respect to the pre-selected point.

Alternatively, polar coordinates may be used to define positions in virtual space with respect to the pre-selected point associated with the tracking system. Alternatively, any other 3D co-ordinate system may be used.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
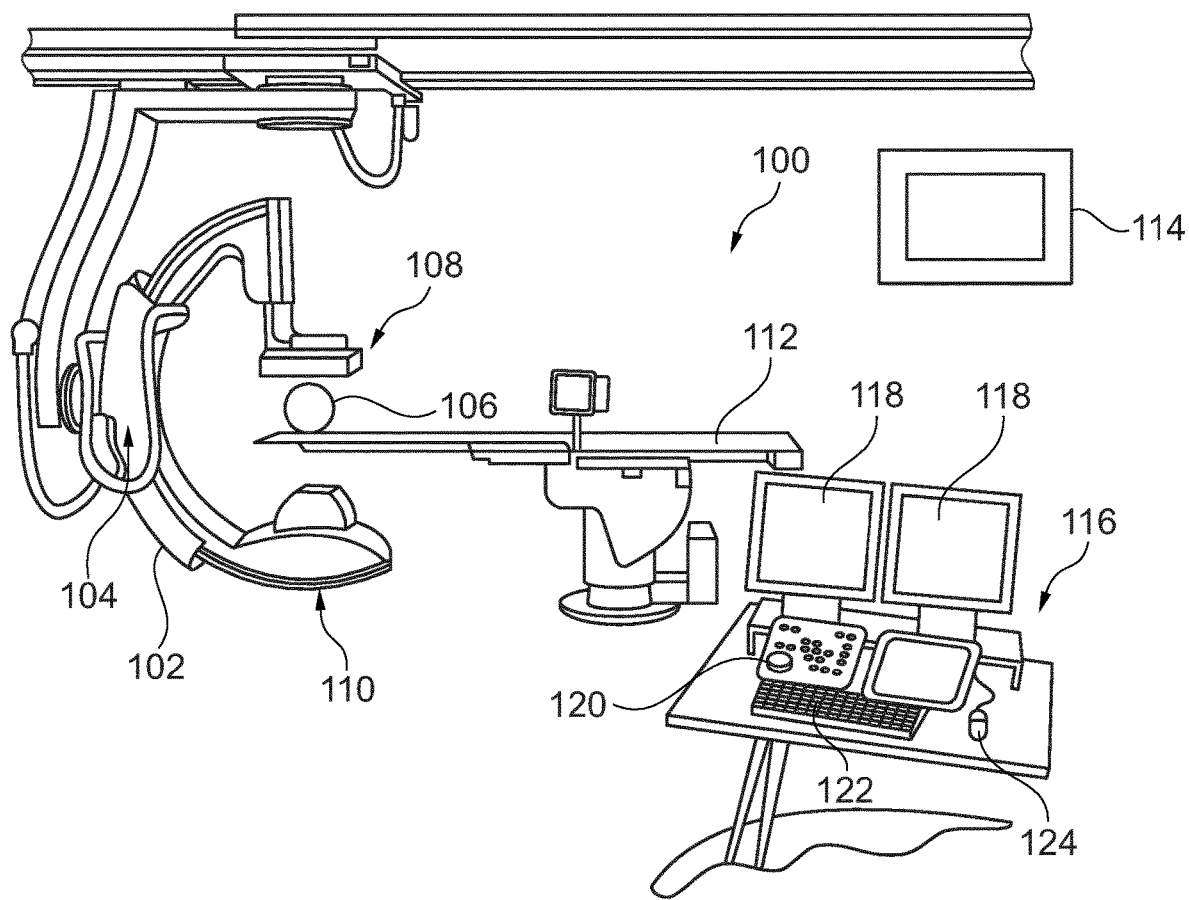
FIG. 1 illustrates a perspective view of an exemplary hybrid operating room (OR) to perform minimally invasive robotic surgical procedures.

In the following, the embodiments are demonstrated in the context of robot-guided pedicle screw placement surgery, but is generalizable to any robotic device positioning application where accurate (e.g., less than 2 mm) positional guidance is required. Examples of the robotic device positioning applications may include, but not limited to, neurosurgery tumor, biopsies, ablations, and many other minimally invasive surgery and percutaneous applications. Further examples of the robotic device positioning applications may include applications in manufacturing and machine operations, such as planes, construction machinery, etc.

Spinal fusion surgery is a common surgical approach to address spinal degenerative disease and spinal deformity, with about 450 thousand procedures performed annually in the US. In a posterior spinal fusion procedure, screws are placed in the pedicles of the vertebra and linked by rods to fuse the vertebrae. For mechanical stability, large diameter screws are desirable. However, maximizing screw diameter in relation to the size of the pedicle may increase the risk of pedicle breach and damage to critical structures such as the spinal nerves, spinal cord or blood vessels. Thus, accurate pedicle screw placement is essential. The current trend towards minimally invasive surgery (MIS), also emphasizes the need for accuracy. MIS is an attractive technique, associated with shorter hospital stays, less post-operative pain, lower-blood loss, lowered risk of infections, and lower-costs4. However, pedicle screw placement in MIS relies heavily on tools for guidance as the small puncture-like incisions provide little or no visual feedback to the surgeon. Commonly, guidance is provided by fluoroscopy, but this has the drawback of radiation exposure to patient and staff as well as providing only 2D views for a 3D targeting task.

Surgical navigation systems provide a way to plan the surgical approach and translate the preoperative plan into intra-operative desired trajectory. Further, such systems visually guide the surgeon (free-hand) in the operative field. However, surgical navigation requires the surgeon to manually keep the instruments aligned with a virtual plan displayed on a screen outside the surgical field while performing the surgical procedure. Robotic aids are naturally suited for this alignment and stabilization task, and there are a number of commercial and academic solution. Compared to free-hand approaches, robotic use results in higher precision in pedicle screw placement, reduced radiation exposure to surgeons, and earlier discharge.

In pedicle screw fixation process, the main assistance provided by the robot is precise alignment of a guide or the instrument with planned trajectory defined in navigation software. Once the instrument (e.g., needle) is aligned with target and firmly held at this alignment by the robot, the surgeon advances a needle or drill to the bone, and further inside of the vertebrae. After the hole is created surgeon places a screw inside these pilot holes and fixes the adjacent screws with rods to fuse multiple vertebrae in a desired configuration.

Robotic solutions typically rely on an external tracking system to locate the robot and to establish a robot to patient (dynamic) reference frame with optical markers fixed rigidly to the patient's spine or iliac crest. These dynamic reference frames tend to be attached far away from the target vertebrae, and are prone to accidental shifts and obstructions, decreasing patient tracking accuracy and increasing the risk of registration errors. Besides occupying considerable space in an often crowded OR, the existing systems require a manual registration step using specialized hardware needed to be installed on the robot or invasively on the patient.

Since the desired tool position is defined in the tracking coordinate system, the robot needs to be tracked, and/or registered to the tracking coordinate system in some way, to enable the transformation of the target positions into its own coordinate frame (CF) for moving the instrument to target trajectory. This is often done with large markers on the robot base, which requires large tracking field of view and adds another transformation between the target and the instrument to be placed. Others add a large 6-DOF device tracking marker and calculate the tracker position through inverse transform of standard kinematics, but this requires multiple calibrations and high precision. Other solutions rigidly fix the robot to the patient or the table and then perform registration steps. These approaches require very good forward kinematics—very high-quality parts, assembly, calibration and general rigidity of the robot and fixation.

FIG. 1 illustrates a perspective view of an exemplary hybrid OR 100 to perform minimally invasive robotic surgical procedures, where a robot may be used for precise alignment of a guide or the instrument with planned trajectory defined in navigation software.

The exemplary hybrid OR 100 is a single room with dedicated C-Arm X-ray imaging system 102 capable of two-dimensional (2D) or three-dimensional (3D) imaging. The C-arm imaging system 102 has a support arrangement 104 which may translate through azimuth and elevation axes around an object of interest 106. For example, the C-arm X-ray imaging system 102 may be supported from the ceiling of an X-ray facility. The support arrangement holds a rotary anode X-ray source 108 and an X-ray detector 110.

The exemplary hybrid OR 100 also comprises a patient support 112 to support the object of interest 106. The C-arm 102 is configured to translate around the object of interest 106, not simply in a flat rotational sense (in the sense of a CT scanner), but also by tilting.

The exemplary hybrid OR 100 typically comprises an external display 114 allowing a surgeon to view the internal surgical site for providing surgical navigation.

The C-arm X-ray imaging system 102 is controlled, for example, from a control console 116, comprising, for example, display screens 118, computer apparatus 120 optionally functioning as a stator control system, controllable via a keyboard 122 and a mouse 124.

A hybrid OR can improve facility utilization by covering many procedures from endovascular to minimally invasive or open surgery; and to enable exploration of new procedures that leverage intra-op high-quality imaging and high-level of device integration. Incorporating robotic guidance into this environment can provide added accuracy by precisely transferring the surgical plan to the patient and streamline surgical workflows. However, this may be challenging due to existing OR equipment, geometric constraints from limited surgical workspace and imaging volumes, and well-established surgical workflows.

For example, for spine surgery in a Hybrid OR, a robotic guidance system for pedicle screw placement may to be quick to set up, low profile, and sterile near the surgical field. In addition, it may need to provide visual access for the surgeon and also for the optical tracking system. The robot may need to reach all the trajectories planned for a given volume without adjusting its base location to minimize workflow disruption. It may also need a rapid and simple method for retraction from surgical field whenever the surgeon is done with it; and to fit under the detector during normal cone beam computed tomography (CBCT) scans, without inducing significant image artifacts. The surgeon should not be required to manually register the reference frames for the surgical plan, the patient tracking, and the robot. The patient tracking should be non-invasive and robust to partial occlusions. Most importantly, the robot should be highly accurate in transferring the navigation plan to the patient (<0.5 mm and <0.5 degrees of the planned trajectory), to minimize pedicle breaches greater than 2 mm, which are clinically unacceptable.

Based on the above requirements, a system is proposed for providing fully integrated intra-op 3D imaging and planning; and automatic alignment of instruments to the planned trajectory using a robot having at least four degrees of freedom of control.

Figure 2:
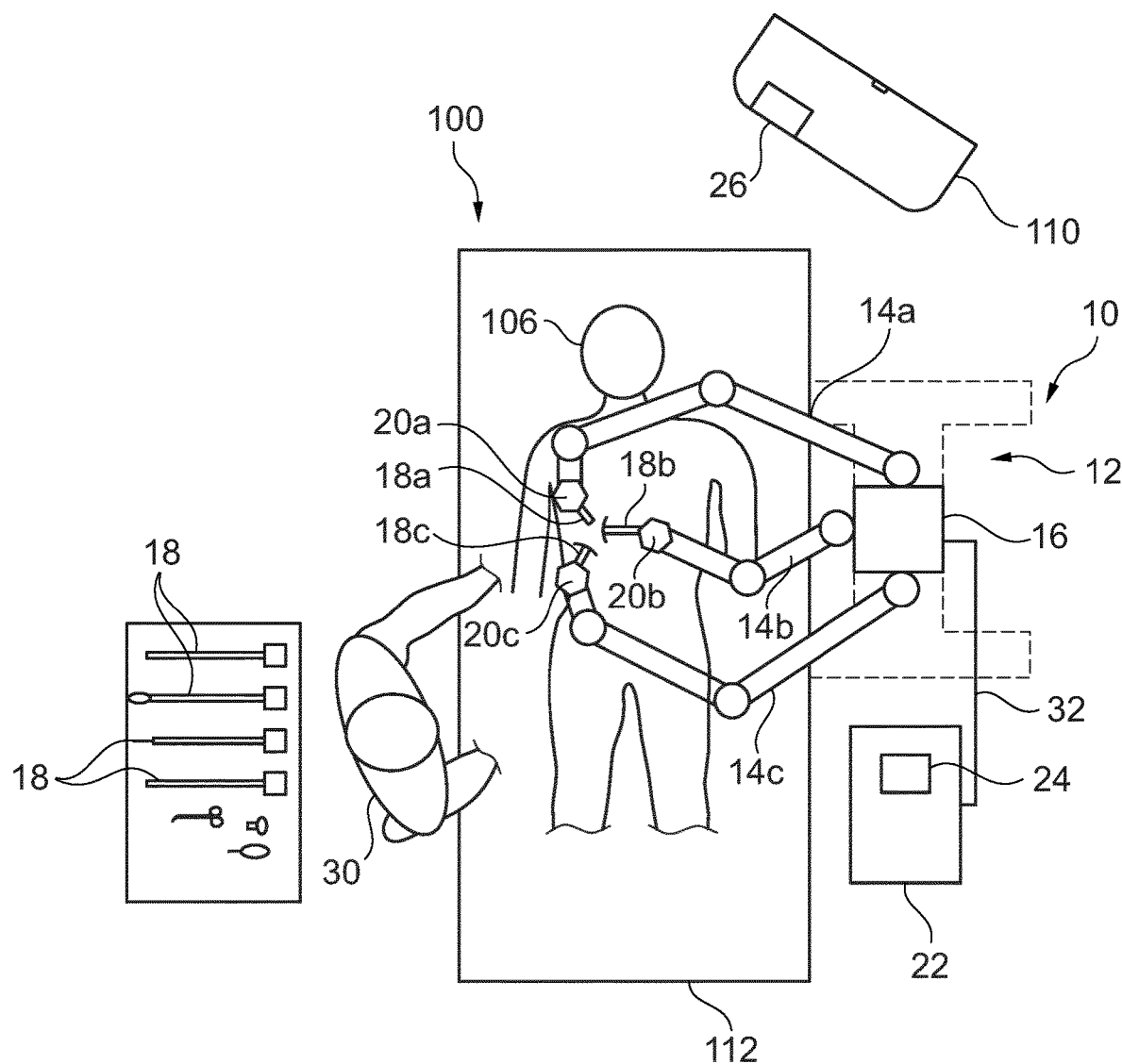
FIG. 2 illustrates a top view of an exemplary system for instrument positioning in an exemplary illustrated hybrid OR according to some embodiments of the present disclosure.

FIG. 2 illustrates a top view of an exemplary system 10 for instrument positioning in the illustrated hybrid OR 100.

The system 10 comprises a robotic system 12 having one or more robotic arms 14, such as robotic arm 14a, 14b, and 14c in FIG. 2. The robotic system 12 may be mounted on the side of a patient support 112, e.g., via a rail-mounting adapter 16, outside of the surgical field. Each robotic arm 14 has four or more degrees of freedom of control. The robotic arm 14 comprises an instrument interface, e.g., a needle guide, connectable to an instrument 18, such as instrument 18a, 18b, and 18c in FIG. 2. As an example, the central robotic arm 14b may support an endoscopic camera 18b. The robotic arms 14a and 14c may support interventional instruments, such as an interventional laser device, that manipulate tissue.

The instrument 18 may be any instrument or tool that is connectable to a robotic arm that can be manipulated thereby. Examples of the instrument 18 may include, but not limited to, surgical tools, medical tools, bio-medical tools, and diagnostic instruments. Surgical tools may include e.g., irrigation and injection needles, tips and tubes, for introducing fluid, scopes and probes (e.g., fiber optic endoscopes and tactile probes), ultrasound tissue disruptors, drills, cryotomes and cutting laser guides. Diagnostic instruments may include e.g., ultrasound instruments, computer tomography (CT) scanner, magnetic resonance imager (MRI).

Figure 4:
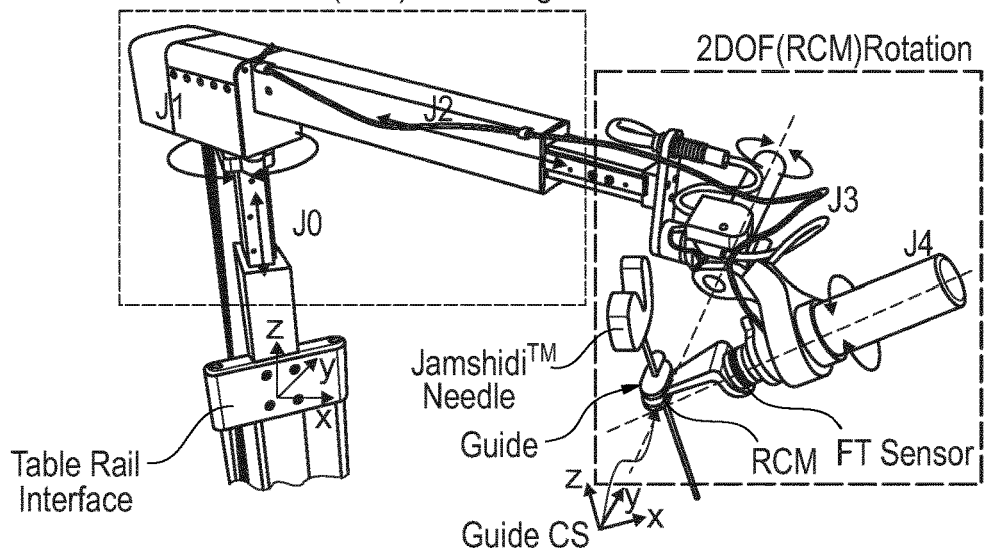
FIG. 4 schematically illustrates an example of a robotic arm.

Generally, the robotic arm 14 may be divided into two modules including a translation module and a rotation module, such as rotation module 20a, 20b and 20c. An example of the two modules is illustrated in FIG. 4. The translation module may be a 3-DOF translation module, which allows the instrument 18 to be translated to an entry point, and then rotated with the rotation module to align.

The system 10 further comprises a system controller 22 with an interface unit 24. For example, the system controller 22 may be the exemplary control console 116 in FIG. 1. The interface unit 24 of the system controller 22 is configured to provide sensor data comprising pose information of the instrument and target position with respect to an object of interest 106. The pose information of the instrument comprises location and orientation of the interventional instrument. The sensor data may be obtained from a tracking system 26. For example, the tracking system 26 may be an optical tracking system comprising one or more cameras or optical sensors, which may be arranged in the hybrid OR for capturing sensor data that comprises pose information of the instrument. Non-invasive disposable passive skin markers may be distributed around the target position, e.g., around surgical incisions, for providing the required occlusion redundancy and tracking robustness. By tracking these markers on the patient during image acquisition, the object coordinate system may be registered to the image coordinate system used for planning and/or the tracking coordinate system. Alternatively or additionally, the tracking system may comprise an electromagnetic tracking system and/or an acoustic tracking system.

For example, for an optical tracking system, markers coated with a retroreflective material can be used to reflect light that is generated near the cameras lens. The camera's threshold can be adjusted so only the bright reflective markers will be sampled, ignoring skin and fabric. Alternatively, fiducial markers can be used. The centroid of the marker is estimated as a position within the two-dimensional image that is captured. The grayscale value of each pixel can be used to provide sub-pixel accuracy by finding the centroid. The position of each of the markers can be used to define the axes of the object coordinate system relative to the tracking coordinate system. The origin of the object coordinate system can be defined arbitrarily and the direction of the axes can be defined based on the positions of the markers around the target position. Thus, the tracking coordinate system can be registered to the object coordinate system based on the positions of the markers (and possibly on the orientation of the markers).

Alternatively, an electromagnetic tracking system could calculate the position and orientation of electromagnetic trackers around the target position by the relative magnetic flux of three orthogonal coils on both a transmitter and receivers. The relative intensity of the voltage or current of the three coils allows electromagnetic tracking systems to calculate both range and orientation by meticulously mapping the tracking volume. Similarly, the tracking coordinate system can be registered to the object coordinate system based on the measured positions and orientations of the markers. Other tracking systems can also be used.

Preferably, as illustrated in FIG. 2, the tracking system 26 may be located on or inside a detector 110 of the image acquisition system. Locating the tracking system on or inside the detector inherently spatially registers the tracking coordinate system to the image coordinate system. This may alleviate the need to e.g. independent track and register the tracking coordinate system of an external tracking system to the image coordinate system. Tracking the instrument 18 in this manner may provide more accurate tracking of the instrument as compared to the use of e.g., shape sensors on the robot whose errors are compounded back to the fixed base of the robot.

The interface unit 24 of the system controller 22 is further configured to provide image data at the target position. The image data may be acquired by an image acquisition system, such as an X-ray imaging device as illustrated in FIG. 1, an ultrasound imaging device, or a magnetic resonance imaging device. A target trajectory 28, e.g., skin entry and target point, is planned by a user 30, e.g., a surgeon, in the image data for positioning the instrument to the target position. For example, an intra-op CBCT acquisition is made, on which the surgeon plans 3D instrument trajectories, such as pedicle screw locations.

The system controller 22 is configured to transfer the pose information of the instrument 18 and the planned target trajectory 28 into an object coordinate system. This is achieved by registering the object coordinate system to the tracking coordinate system and the image coordinate system. Many methods exist which will be known to a person skilled in the art. One of these methods includes using the tracking system with markers on the object and the instrument as previously described.

The system controller 22 is further configured to calculate a positional error between the tracked pose information of the instrument and the planned target trajectory. The positional error comprises at least one of a translational error and a rotational error. The error metric for alignment is the angle between the target and the trajectory, while the translational alignment is the length of the vector from instrument to the target trajectory vector.

Figure 3A:
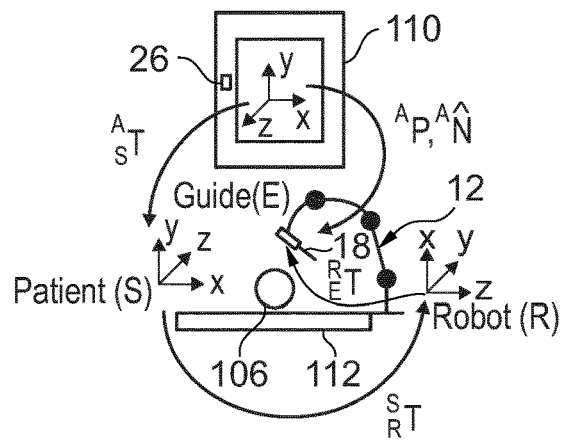
FIG. 3A illustrates an example of coordinate frames in the system for instrument positioning.

FIG. 3A illustrates an example of coordinate frames in the system 10. Target and entry are defined in the object coordinate system. In the illustrated example, the object coordinate system may also be referred to as patient coordinate system. The tracked pose information of the instrument may comprise location of the instrument tip ($P_D$) and its principal axis ($\hat{N}$). The target trajectory may be defined by the skin entry point ($P_E$) and the target point ($P_O$) inside of the pedicle, corresponding to the planned screw trajectory. All these are transformed into the patient coordinate system (S). The main assumption is that the instrument axis is co-linear with the robot guide axis, and that the patient reference is not moved significantly relative to the robot base during the targeting session.

Figure 3B:
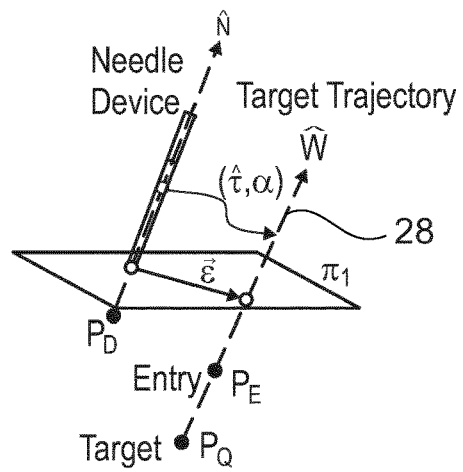
FIG. 3B illustrates an example of an error metric for alignment.

FIG. 3B illustrates an example of an error metric for alignment. The error metric for alignment is the angle between the target and the trajectory, while the translational alignment is the length of the vector from instrument to the target trajectory vector, in a safety plane $^R\pi_1$ defined by XY plane of the robot and the current robot guide position. Alternatively, the safety plane location may be defined as: relative to the tip of the instrument, and then transformed into the robot coordinate system, relative to the closet point on the instrument to the target trajectory with some reasonable constraints, such that point is not too far from the robot guide, or relative to the entry point.

In FIG. 3B, $\vec{\varepsilon}$ is the translation from device axis to target trajectory axis in plane $\pi_1$, ($\vec{\tau}$, $\propto$) is the 3-DOF rotation (Axis-Angle) between the device axis and the target trajectory axis.

The system controller 22 is configured to transfer the positional error into a robot coordinate system of the robotic system for controlling the robotic arm to align the instrument with the planned target trajectory. For example, as illustrated in FIG. 2, the system controller 22 may direct movement of robotically controlled instruments 18a-18c via control lines 302 effecting movement of the instruments to align the instrument with the planned target trajectory using the one or more robotic arms 14.

In operation, the object of interest 106, e.g., a patient, is delivered and prepared for surgery. An intra-op CBCT acquisition is made, on which a user 30, e.g., a surgeon, plans 3D instrument trajectories, such as pedicle screw locations. A plan trajectory including skin entry and target points is translated to physical patient space and made available to the robotic system along with the instrument tracking. The pose information of the instrument is used by the system controller 22 for automatic alignment to the target defined in patient coordinate system. Once aligned, the robot holds position and the surgeon hammers the instrument into the pedicle to make a pilot hole into which a screw is placed. The surgeon can manually move the robotic arm away from the surgical site by enabling "swing-arm" mode, or leave it in place for additional guidance or verification imaging.

Accordingly, by extending the robotic arm 14 into the surgical field, the system 10 can automatically align the instrument 18 following the surgical plan using only instrument tracking feedback; no tracking markers on the robotic arm 14 are required. The proposed system may provide an accurate and workflow friendly robotic guidance system e.g., for creating pedicle screw pilot holes in spine fusion procedures: The robotic arm precisely aligns the instrument with the desired trajectory, and the surgeon hammers or drills the instrument into the pedicle. The system controller uses a servo control method to achieve high alignment accuracy relying only on e.g., 4-DOF or 5-DOF instrument tracking feedback and no manual robot registration steps are required.

Optionally, the sensor data comprises pose information of the robotic arm. This may allow a hybrid feedback control that includes both robot end-effector tracking and instrument tracking feedback. This may allow for rough alignment with less precise robot tracking even without the instrument in the guide, and once the device is visible in the tracking system and is near the target trajectory, the proposed system can be used to servo for final high-accuracy alignment.

Robot System

FIG. 4 schematically illustrates an example of a robotic arm 14. The robot arm 14 may feature five active joints, and a sixed passive rotation inside a single axis instrument guide as the end-effector. The exemplary robotic arm 14 is divided into two modules. The 3-DOF translation module includes vertical linear stage (J0), shoulder revolute joint (J1), and horizontal linear stage (J2). It carries the 2-DOF rotation module: a mechanical Remote-Center-of-Motion (RCM) mechanism. In some examples (not shown), aligning to a predefined plane (e.g., 4-DOF) may be sufficient and thus it may carry 1-DOF rotation module for these examples. The RCM may comprise two spherical linkages: J3 and J4, both of which have angles of 65°, with J3 mounted at 60° to vertical. This serial kinematic architecture is chosen to satisfy the minimal number of degrees required to position a needle like instrument in Cartesian space. The inclusion of an RCM may minimize overall joint motions, producing ergonomic robot configurations and predictable motions for improved user experience, especially when executing Cartesian rotations. It allows the instrument to be translated to an entry point, by predominantly actuating the first three joints, and then rotated to align, using only the two distal (RCM) joints. The last link shape is optimized so the instrument guide is closer to the RCM, enabling guide positioning closer to the skin-incision, to improve precision of trajectory transfer to the patient and facilitate the use of short instruments.

The robotic system 10 may include a rail-mounting adapter 16 that can attach to standard OR table rails, or rails integrated into a custom plate placed under the patient to provide rigidity and positional flexibility. The link lengths and spherical linkage angles provide sufficient coverage for at least 6 levels, and ±60° to cover unusual trajectory angles beyond the healthy patient's range of −14° to 20° in sagittal plane, and ±22° to 35° in the transverse plane. The last link allows installation of variable diameter guides that can lock an instrument in place or provide lateral exit functionality. The robot body prototype was machined out of aluminum channels and 3D printed in case of non-structural members. Common off-the-shelf mechatronic components were used for motors and transmissions. A 6-DOF Force Torque (FT) sensor may be integrated into the last link of the robot to provide FT measurements at the instrument guide. The FT is used for admittance (hands-on positioning) control method and monitoring loads in the guide during the intervention. It provides GUI, forward/inverse kinematics, and various control modes (force control, ARSN align servo, remote joystick, insertion, etc.). A joystick may be used for remote positioning input, to trigger automatic alignment, and enable hands-on positioning mode. In some embodiments, the FT interface can also be used to trigger the automatic alignment by detecting when the user is holding the instrument guide. Once the guide is not held anymore, the auto-alignment will stop.

System Controller

The system controller 22 may be controlled by a trajectory-alignment algorithm to align the instrument with the planned target trajectory 30. The goal of the trajectory-alignment algorithm is to align the instrument with the planned target trajectory, with the highest possible precision while not adding any additional (registration) steps to the surgeon's workflow. For an instrument having a 4-DOF or 5-DOF, the instrument tracking feedback may be inherently insufficient for 6-DOF Cartesian robot positioning without a precise coordinate system (CS) registration, especially since the exact location, e.g., depth, of the instrument inside the instrument interface is unknown.

For an instrument that has an elongated shape, the proposed system controller 22, without a 6-DOF reference body on the robot, may be configured to control the robotic arm during a first motion of the robotic arm for each new targeting session to move the instrument in a predefined movement to generate a rough six degrees of freedom registration between the object coordinate system and the robot coordinate system. The predefined movement comprises a predefined rotational movement and, optionally, may also comprise a predefined translational movement. Generally, assuming the motion of the robotic system and the instrument tracking feedback can be synchronized precisely, the predefined rotational movement for rough registration may be arbitrary, as long as it includes a large rotation, as larger angles lead to more accurate registration. It may also be possible to add arbitrary translation as well. This feature may be used in real-time to update or verify that the registration has not changed due to patient movement relative to the robotic system.

For example, referring now to FIG. 3B, to generate the rough registration ($_R^S T$) the tracked needle is fixed in guide (to prevent sliding down), upon commanding alignment to the first target in the targeting session, the robot begins motion by e.g., rotating 15 degrees about its RCM in a predefined direction (towards the opposite side of table). Of course, the robot may also begin motion by rotating other degrees about its RCM in a predefined direction, such as 5 degrees, 10 degrees, 20 degrees, 30 degrees, 40 degrees, 50 degrees, 60 degrees, 70 degrees, 80 degrees, or 90 degrees. Two robot poses ($_R^S T_1$ and $_R^S T_2$) and two needle positions ($^S N_1$, $^S N_2$) are collected before and after the movement, and $_R^S T$ is then calculated using a temporary coordinate system (D). As a reminder, the patient coordinate system is referred to as (S) and the robot coordinate system is referred to as (R). The rough registration ($_R^S T$) is calculated as follows:

Translation component ($^S P_D$) is determined by calculating the closest point between two line vectors representing the needle axis ($^S N_1$, $^S N_2$,) using least squares approach which corresponds to the robot's RCM location ($^R P_{RCM} = ^R P_D$).

Rotation component of ($^S_D R$) is created from the two line-normals) ($^S \hat{N}_1$, $^S \hat{N}_2$) using the standard cross product method. The same is done for $_D^R R$ from the robot guide z-axis normal ($_G^R \hat{Z}_1$, $_G^R \hat{Z}_2$).

The (object) registration between the patient coordinate system and the temporary coordinate system is referred to as $_D^S T$.

The (robot) registration between the robot coordinate system and the temporary coordinate system is referred to as $_D^R T$.

The registration between the patient coordinate system and the robot coordinate system is referred to as $_R^S T$.

The $_D^S T$ and $_D^R T$ are constructed from [$_D^S R$, $^S P_D$] and [$_D^R R$, $^R P_D$] respectively. Then $_R^S T$ is simply $_D^S T \cdot _D^R T^{-1}$.

The resulting registration process may take a few seconds and may be sufficient for positioning of the instrument near the desired trajectory in open loop fashion e.g., when outside of the tracking volume, but due to limited registration data, and small robot inaccuracies may be not sufficient for precise alignment.

For precision alignment, real-time needle position feedback may be used to iteratively move the needle mounted in the guide to align with the target trajectory. Once aligned, the surgeon could lower the robot along the guide axis (by force control with insert-along-axis constraint) and if needed, command robot to align-to-target.

Optionally, the sensor data may comprise real-time pose information of the instrument with respect to the target position. Optionally, the height of the robotic guide, i.e. instrument interface, is kept constant during the alignment. The height constraint may provide safer and more intuitive robot behavior. The system controller may be configured to calculate a real-time positional error between the tracked pose information of the instrument and the planned target trajectory and transfer the real-time positional error into the robot coordinate system of the robotic system for iteratively controlling the robotic arm to align the instrument with the planned target trajectory.

For example, referring now to FIG. 3B, the goal position of the guide in the robot coordinate system ($_G^R T$) for each iteration may be calculated in the following manner:

Consider the plane $^R \pi_1$ defined by XY plane of the robot ($^R[0,0,1]^T$) and the current robot guide position $^R P_{RCM}$.

Compute $^R P_{Q1}$, the intersection between the target line ($^R P_Q$, $^R \hat{W}$) and $^R \pi_1$; and $^R P_{N1}$, the intersection of the needle axis line and $^R \pi_1$.

The displacement error vector is $^R \vec{\varepsilon} = ^R P_{Q1} \Delta^R P_{N1}$, then goal translation ($^R P_G$)=$^R P_{RCM}+^R \vec{\varepsilon}$. Since $^R P_{Q1}$ and $^R P_{N1}$ lie on the XY plane (nearly parallel to the table) of the robot coordinate system, the robot's guide translation is only in this plane.

The rotational error is calculated in the robot guide frame by creating an axis-angle rotation between the needle axis $^E \hat{N}$ and target trajectory axis $^E \hat{G}$: $\hat{\tau} = ^E \hat{N} \times ^E \hat{G}$; and the angle between them is $\alpha$.

Normalize $\tau$, then set $\hat{\tau}_z$ to 0.0 and normalize again.

This removes the rotation about the $^E R_{\hat{z}}$, since it is arbitrarily defined due to 4-DOF or 5-DOF target and instrument definitions, besides the robot can't perform such a rotation.

The desired goal is $_G^R R = _E^R R \ _G^E R$, where $_G^E R$ is the approximate rotational error [$\tau$, $\alpha$] represented as a rotation matrix.

The rotation and translation goals are combined into a single homogenous transform [$^R R_G$, $^R G$] and sent to the robot position controller.

Each servo iteration may be performed after the previous robot command was complete. In a typical setting, less than 5 iteration steps are required for the robot to align the tracked needle with the target to within $^R \vec{\varepsilon}$ <0.25 mm and $\alpha$<0.25° error tolerance.

Optionally, the safety plane $^R \pi_1$ defined by XY plane of the robot ($^R[0,0,1]^T$) and the current robot guide position P$^R_{RCM}$ may be updated at each iteration defined by a mesh of triangles, where each triangle defines the plane that the robot can translate on. The mesh may be an offset, e.g., 5 cm, from patient surface model, constraining the motion of the robot to this offset. Such model may be approximation from the stickers placed on the patient.

In some examples, the system controller 22 may compute an approximate registration and interactively control the robot towards the target in two distinct steps. Alternatively, the system controller 22 may simultaneously drive the robot system to the target while continuously updating/improving the registration between the object coordinate system and the object coordinate system.

Figure 5:
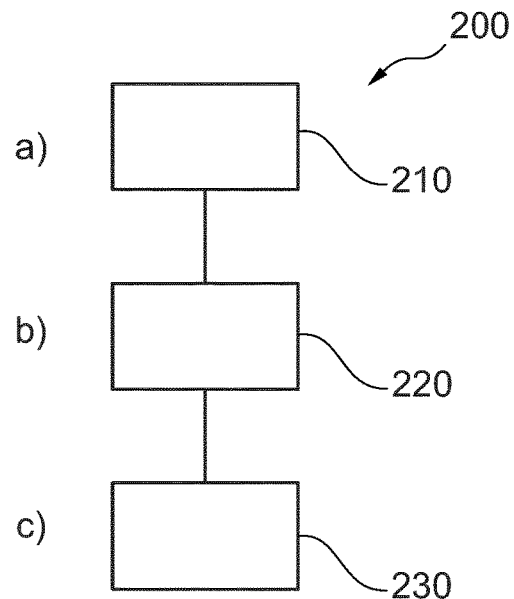
FIG. 5 illustrates a flow diagram of a method of controlling a system according to some embodiments of the present disclosure.

FIG. 5 illustrates a flow diagram of a method 200 of controlling a system as described above and below according to some embodiments of the present disclosure. The method comprises the following steps:

In step 210, i.e. step a) , sensor data is received by an interface unit of a system controller of the system. For example, there is provided a tracking system, such as an optical tracking system, to obtain the sensor data and transmit the obtained sensor data to the system controller. The sensor data comprises pose information of an instrument with respect to a target position relative to an object. The pose information of the instrument comprises location and orientation of the interventional instrument.

In step 220, i.e. step b), image data at the target position is received by the interface unit of the system controller. A target trajectory is planned in the image data for positioning the instrument to the target position. Step a) and step b) may be performed in various orders, such as a)→b), b)→a), or a) and b) simultaneously.

In step 230, i.e. step c) , the pose information of the instrument and the planned target trajectory are transferred by a system controller of the system, into an object coordinate system. A positional error between the tracked pose information of the instrument and the planned target trajectory is calculated. The positional error is transferred into a robot coordinate system of the robotic system for controlling the robotic arm to align the instrument with the planned target trajectory. The positional error comprises at least one of a translational error and a rotational error.

Figure 6:
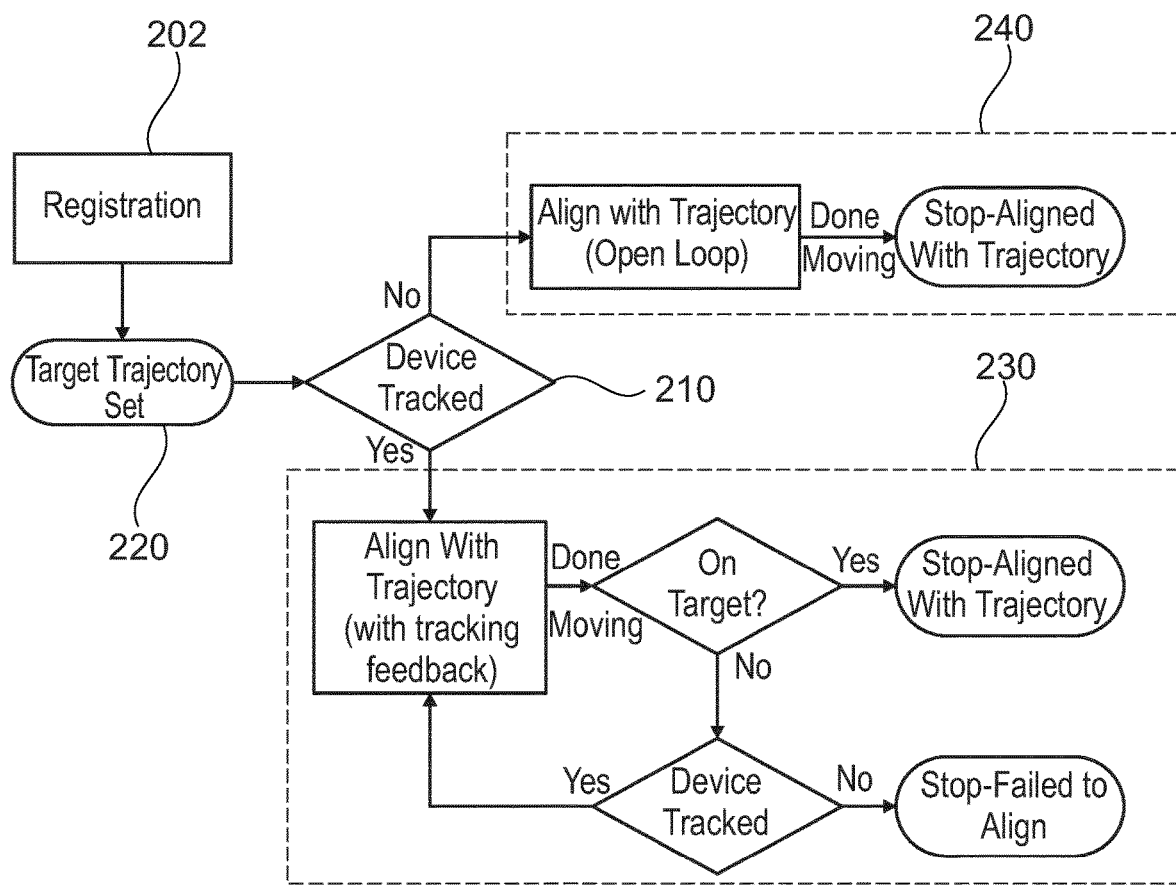
FIG. 6 illustrates a flow diagram of a method of controlling a system according to some other embodiments of the present disclosure.

FIG. 6 illustrates a flow diagram of a method 200 according to some other embodiments of the present disclosure. In the method 200, a rough registration step 202 may be provided before steps 210 to 230 for instruments having an elongated shape. In this step, during a first motion of the robotic arm for each new targeting session, the robotic arm is controlled to move the instrument in a predefined movement to generate a rough six degrees of freedom registration between the object coordinate system and the robot coordinate system. The predefined movement comprises at least one of a predefined translational movement and a predefined rotational movement. The first motion of the robotic arm automatically initiates the rough registration process. Accordingly, the system controller may perform the rough registration automatically, avoiding any input from a user or adding time to the procedure. The resulting registration process may take a few seconds and may be sufficient for positioning of the instrument near the desired trajectory in open loop fashion e.g., when outside of the tracking volume, but due to limited registration data, and small robot inaccuracies may be not sufficient for precise alignment.

In other words, with the registration process 202, the method may further comprise step 240. In this step, the instrument is aligned with the planned target trajectory based on the rough six degrees of freedom registration between the object coordinate system and the robot coordinate system. In other words, the rough six degrees of freedom registration is used to position the instrument near the desired trajectory in open loop fashion e.g., when outside of the tracking volume. Once the instrument is detected, e.g. when inside the tracking volume, step 230 may be performed.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for instrument positioning, comprising:
a robotic system with a robotic arm having four or more degrees of freedom, DOF, of control; and
a system controller with an interface unit;
wherein the robotic arm comprises an instrument interface connectable to an instrument;
wherein the instrument has an elongated shape;
wherein the interface unit of the system controller is configured to provide sensor data comprising pose information of the instrument and target position with respect to an object of interest, wherein the pose information of the instrument comprises location and orientation of the instrument;
wherein the interface unit of the system controller is further configured to provide image data at the target position, wherein a target trajectory is planned in the image data for positioning the instrument to the target position and wherein the target trajectory is defined by a skin entry point and the target point; and
wherein the system controller is configured to:
transfer the pose information of the instrument and the planned target trajectory into an object coordinate system;
calculate a positional error between the tracked pose information of the instrument and the planned target trajectory;
control the robotic arm during a first motion of the robotic arm for each new targeting session to move the instrument in a predefined movement to generate a rough six degrees of freedom registration between the object coordinate system and a robot coordinate system based on pose information before the movement and pose information after the movement for each of the instrument and the robotic arm, wherein the predefined movement comprises a predefined rotational movement; and
transfer the positional error into the robot coordinate system of the robotic system for controlling the robotic arm to align the instrument with the planned target trajectory, wherein the positional error comprises at least one of a translational error and a rotational error.

2. The system according to claim 1, wherein generating a rough six degree of freedom registration between the object coordinate system and the robot coordinate system is based on:
collecting two robot poses and two instrument positions before and after the predefined movement;
determining an instrument translation component based on calculating the closest point between two line vectors representing the instrument axis from the instrument positions before and after rotation using the least squares approach;
creating an instrument rotation component from the normal of the two instrument line vectors using the standard cross product method;
creating an object registration between the object coordinate system and a temporary coordinate system based on the instrument translation component and the instrument rotation component, wherein the temporary coordinate system corresponds to the robot's center of motion, RCM;
determining a robot translation component based on calculating the closest point between two line vectors representing the robot axis from the robot poses before and after rotation using the least squares approach;
creating a robot rotation component from the normal of the two robot line vectors using the standard cross product method;
creating a robot registration between the robot coordinate system and the temporary coordinate system based on the robot translation component and the robot rotation component; and generating a rough six degree of freedom registration between the object coordinate system and the robot coordinate system based on the object registration and the robot registration.

3. The system according to claim 1,
wherein the sensor data comprises real-time pose information of the instrument with respect to the target position; and
wherein the system controller is configured to calculate a real-time positional error between the tracked pose information of the instrument and the planned target trajectory and transfer the real-time positional error into the robot coordinate system of the robotic system for iteratively controlling the robotic arm to align the instrument with the planned target trajectory.

4. The system according to claim 1,
wherein the system controller is further configured to apply the rough six degrees of freedom registration for controlling the robotic arm to align the instrument with the planned target trajectory, when the sensor data does not comprise the pose information of the instrument.

5. The system according to claim 1, further comprising:
a tracking system configured to obtain the sensor data comprising the pose information of the interventional instrument and the target position of the object of interest;
wherein the tracking system comprises at least one of:
an optical tracking system;
an electromagnetic tracking system; and
an acoustic tracking system.

6. The system according to any one of claim 5,
wherein the tracking system is located on or inside a detector of the image acquisition system.

7. The system according to claim 1, further comprising:
an image acquisition system configured to acquire the image data at the target position of the object of interest;
wherein the image acquisition system comprises at least one of:
an X-ray imaging device;
an ultrasound imaging device; and
a magnetic resonance imaging device.

8. The system according to claim 1,
wherein the robotic arm comprises a mechanical Remote-Center-of-Motion, RCM, mechanism having at least one degree of freedom of rotational control; and
wherein the instrument interface is mounted on the RCM mechanism.

9. The system according to claim 1,
wherein the system controller is configured to control the robotic arm to align the instrument with the planned target trajectory while the instrument translating in a safety plane for preventing collisions.

10. The system according to claim 1,
wherein the sensor data comprises pose information of the robotic arm.

11. The system according to claim 1,
wherein the instrument comprises an interventional instrument.

12. The system according to claim 11,
wherein the interventional instrument comprises at least one of:
an injection needle;
an interventional catheter; and
an interventional laser device.

13. A method of controlling a system according to claim 1, comprising the following steps:
receiving, by an interface unit of a system controller of the system, sensor data comprising pose information of an interventional instrument with respect to a target position relative to an object of interest, wherein the pose information of the instrument comprises location and orientation of the instrument;
receiving, by the interface unit of the system controller, image data at the target position, wherein a target trajectory is planned in the image data for positioning the instrument to the target position and wherein the target trajectory is defined by a skin entry point and the target point; and
transferring, by a system controller of the system, the pose information of the instrument and the planned target trajectory into an object coordinate system, calculating a positional error between the tracked pose information of the instrument and the planned target trajectory;
controlling a robotic arm during a first motion of the robotic arm for each new targeting session to move the instrument in a predefined movement to generate a rough six degrees of freedom registration between the object coordinate system and a robot coordinate system based on pose information before the movement and pose information after the movement for each of the instrument and the robotic arm, wherein the predefined movement comprises a predefined rotational movement during which movement the instrument is not positioned in a living body; and
transferring the positional error into a robot coordinate system of the robotic system for controlling the robotic arm to align the instrument with the planned target trajectory, during which alignment the instrument is not positioned in a living body, wherein the positional error comprises at least one of a translational error and a rotational error.

14. A non-transitory computer program element for controlling an apparatus, which, when being executed by a processing unit, is adapted to perform the method of claim 13.

15. A non-transitory computer readable medium having stored the program element of claim 14.

* * * * *